United States Patent [19]

Hansen

[11] Patent Number: 4,808,175

[45] Date of Patent: Feb. 28, 1989

[54] DISPOSABLE DIAPER AND WET WIPE PAD PACKAGE

[76] Inventor: William T. Hansen, 5877 S. Kyle Dr., Kearns, Utah 84118

[21] Appl. No.: 78,586

[22] Filed: Jul. 27, 1987

[51] Int. Cl.⁴ ............................................. A61F 13/16
[52] U.S. Cl. ................................................. 604/385.1
[58] Field of Search .................... 604/385.1, 386, 387, 604/358, 389, 390

[56] References Cited

U.S. PATENT DOCUMENTS

| | | | |
|---|---|---|---|
| 3,369,545 | 2/1968 | Wanberg | 604/385.1 |
| 4,221,221 | 9/1980 | Ehrlich | 604/385.1 X |
| 4,417,894 | 11/1983 | Norris | 604/385.1 |

Primary Examiner—John D. Yasko

Attorney, Agent, or Firm—Philip A. Mallinckrodt; Robert R. Mallinckrodt

[57] ABSTRACT

A disposable diaper is combined with a reversible bag provided with coactive sealing members bordering and tightly sealing its otherwise open entrance mouth and protectively containing one or more wet wipe pads for use in cleaning an infant following soiling of the diaper. The bag is attached to one panel face of the diaper, either to or as the usual moisture proof backing for the diaper, and is reversible to encompass the soiled diaper and wet wipe pad or pads after use and bundling together. The coactive sealing members are reversibly arranged for ultimately sealing the bag against release of odor. Double tongue members back-to-back on a flexible plastic sheet to be connected to a second plastic sheet provided with tongue-receiving groove members back-to-back constitute an aspect of the invention having broad areas of use.

8 Claims, 1 Drawing Sheet

DISPOSABLE DIAPER AND WET WIPE PAD PACKAGE

BACKGROUND OF THE INVENTION

1. Field

The invention is in the field of disposable diapers individually combined with a moisture proof envelope providing both a moisture proof backing for the diaper while being worn and a disposable bag into which the soiled diaper is inserted for disposal.

2. State of the Art

The prior art in this field is exemplified by U.S. Pat. No. 4,085,753 of Apr. 25, 1979 entitled "Disposable Diaper with Integral Disposal Bag". Although no provision is made for sealing the bag after reversal of the bag and insertion of the soiled diaper therein, U.S. Pat. No. 4,581,027 of Apr. 8, 1986 entitled "Sanitary Napkin with Means for Disposal" discloses a somewhat similar arrangement of a sanitary napkin with integral disposal bag having a longitudinal slot centrally of the outer panel of the bag which is bordered by adhesive applied to the slit-defining margins of the bag. The thus packaged sanitary napkin is protected until used by an elongate strip applied to the adhesive-coated areas of the bag and removed prior to use of the napkin so the latter can be adhered to a garment of the wearer in usual manner. Following use, the bag is reversed to encompass the solid napkins, and the adhesive, now on the underside of the slit-defining margins of the bag, adheres to the napkin and to an overlapped marginal part of the bag to seal the bag closed about the soiled napkin awaiting disposal.

SUMMARY OF THE INVENTION

It has become standard practice in the use of diapers to have handy at clean-up time a jar of wet wipe pads when removing the diaper. In accordance with the present invention, a disposable diaper is equipped with an integral disposal bag initially containing one or more wet wipe pads and provided with means for sealing the bag opening, thereby retaining the wet wipe pads in usable condition until used and preventing access by the infant wearing the diaper. The disposal bag is reversible, as is the sealing means, whereby the reversed bag is used to receive both the soiled diaper and the soiled wet wipe or pads and is then resealed.

The sealing means may be of any operable type, but is preferably of elongate rib-and-receiving-groove type commonly used on plastic film sandwich or refrigerator bags, but here of double formation so as to be operable initially to seal the packaged wet wipe pad or pads and subsequently when the bag is reversed to seal such bag that now contains the soiled diaper and soiled wet wipe pad or pads.

THE DRAWING

The best mode presently contemplated for carrying out the invention in actual practice is illustrated in the accompanying drawing in which:

FIG. 1 is a plan view looking toward the inner surface of a disposable diaper embodying the invention as extended for immediate use;

FIG. 2, a fragmentary section taken on the line 2—2 of FIG. 1 and drawn to a considerably larger scale;

FIG. 3, an elevational view of the wet wipe bag as turned inside out and containing, in sealed condition, the diaper and wet wipes in soiled condition and folded over the soil;

FIG. 4, a section corresponding to that of FIG. 2 but taken on the line 4—4 of FIG. 3; and FIG. 5, a fragmentary view corresponding to the upper end portion of FIG. 4 but showing a somewhat different embodiment of the invention in which only single interacting sealing members are provided and sealing in the reversed bag mode is effected by reverse folding of the bag edge margins.

DETAILED DESCRIPTION OF ILLUSTRATED EMBODIMENTS

Figure 1:
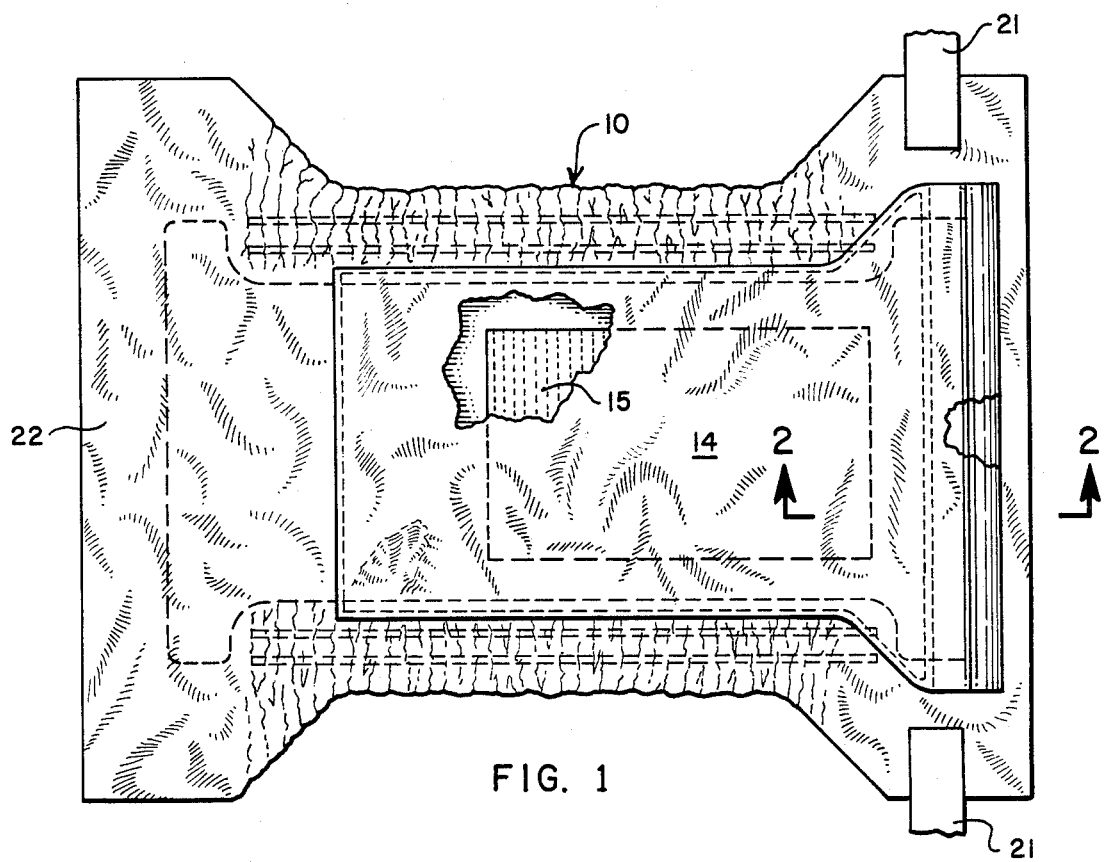

In the form illustrated in FIGS. 1-4, a disposable diaper 10 of standard construction having a filling 10a of soft absorbent material and a body-contacting interior panel 10b of soft absorbent material, has a moisture proof backing panel 11 fastened, as by adhesive 12, to a broad panel wall 13 of a moisture proof and odor impermeable bag 14 which contains one or more wet wipe pads 15 of usual premoistened type. The mouth opening 16 of the bag is tightly sealed against loss of moisture from the pads.

Sealing means of any suitable type may be employed, having due regard for the fact that the bag 14 must be resealed following its being turned inside out after the soiling and the removal of the diaper from an infant and after use of the wet wipe or wipes 15 originally sealed in the bag.

Considering the fact that bag 14 is normally made of an impermeable but flexible plastic sheet material, an easily used and effective sealing means is of the elongate tongue and groove type commonly employed for sandwich bags or refrigerator bags, as shown generally at 17. Both the torque member 18 and the groove member 19 are advantageously made double, back-to-back at opposite margins of the panel walls concerned. Thus, as shown, double tongue members 18 are provided on opposite opening edge margins of bag wall 13 adjacent to mouth 16 and double groove members 19 are provided on opposite opening edge margins of the opposite bag wall 20.

Figure 2:
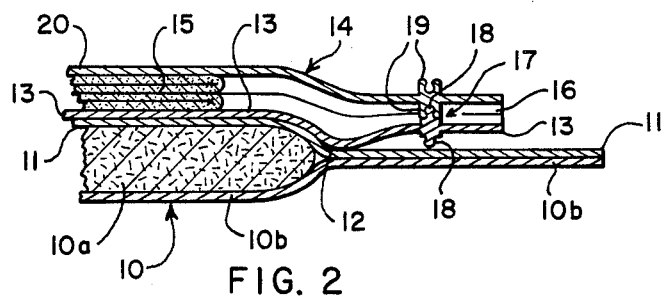

A tongue member 18 and a groove member 19 initially confront each other within mouth opening 16 of bag 14 and seal tightly together, as shown in FIG. 2, to protect wet pad or pads 15 in the bag for marketing and storage purposes. They are pulled apart when opening the bag to remove such pad or pads for use after the infant wets the diaper or has a bowel movement.

Figure 3:
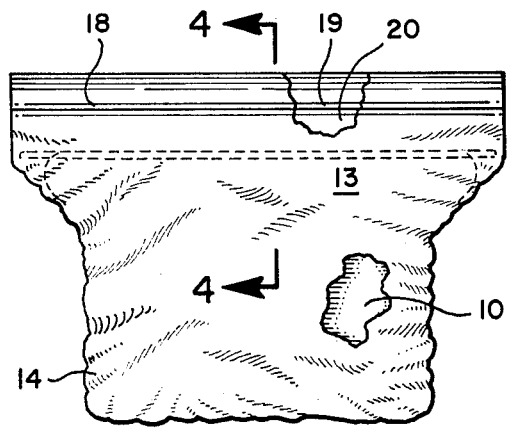

Diaper 10 is applied to and removed from the infant in the usual manner using the usual adhesive tabs 21 or other securing means provided. Following removal, the diaper is folded upon itself to cover the soil and the soiled pad or pads that are placed thereon after the wiping operation and to make them into a relatively compact bundle. This can be easily done without touching the soiled portion of the diaper or the soiled pad or pads. Bag 14, which is now open, is turned inside out over the bundled diaper. This brings the other tongue 18 and the other groove 19 into confronting relationship for reversed bag sealing as shown in FIGS. 3 and 4.

Figure 4:
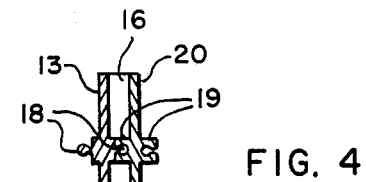

The flap end 22 of diaper 10 opposite the mouth end of the bag may be folded under the sealed mouth opening 16 of the bag as shown in FIG. 4 to provide added protection against the escape of odor from the sealed bag awaiting disposal of such sealed bag in the usual manner.

It may be desirable, in some instances, to construct the diaper to include bag wall 13 in place of diaper backing panel 11 so that the bag is integrated with rather than being attached to the diaper.

Figure 5:
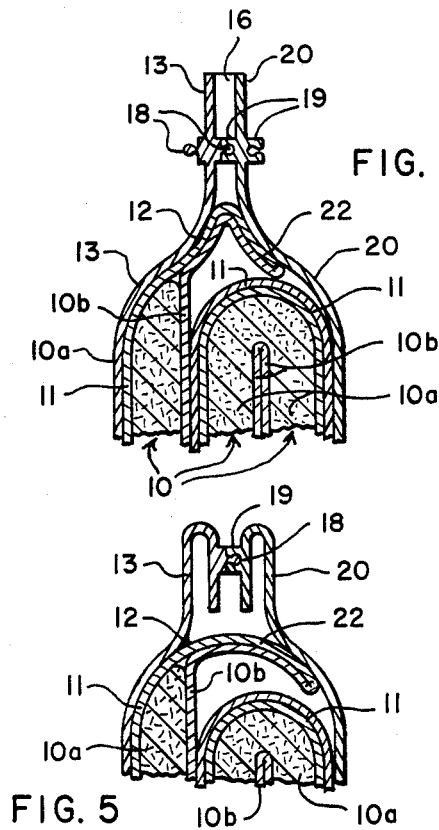

Other sealing arrangements may be employed even with the tongue and groove type. Thus, a single set of tongue member 18 and groove member 19 may be provided on the inner faces, respectively, of bag wall 13 and bag wall 20 so as to initially seal bag 14 in the unused wet wipe pad mode of FIG. 2. After turning bag 14 inside out over the bundled soiled diaper and soiled wet wipe pads, the sealing members will be on the outside faces of the bag side walls and may be brought into interacting relationship by folding the bag wall edge margins on which such backing members are located inwardly of the open mouth of the reversed bag and fitted together in sealing relationship as shown in FIG. 5. In this arrangement, the portions of the wall edge margins that project beyond the tongue and groove members may be shortened from what is shown in FIGS. 1 and 4 to facilitate the reverse sealing operation.

In other sealing arrangements, various interacting sealing members may be employed. For example, adhesive strips such as employed in the sanitary napkin package of the aforementioned Alvarado U.S. Pat. No. 4,581,027 could be used in place of the tongue and groove members 18 and 19, respectively. Either of the foregoing arrangements of locking members would be operable here as with the tongue and groove type.

One aspect of the invention having broader implications than use solely in diapers is the reversible sealing means employed having a double tongue member 18, 18, FIGS. 2-4, and a double, receiving groove member 19, 19, FIGS. 2-4, each double member being formed back-to-back on opposite faces, respectively, of a pair of plastic sheets (13 and 20) to be connected in sealing relationship.

Whereas this invention is here illustrated and described with specific reference to the embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A disposable diaper and wet wipe pad package, comprising a disposable diaper; a reversible, moisture proof bag having oppositely positioned broad panel walls, one of which is fastened to said diaper as a moisture proof backing therefor, said bag having an opening positioned to receive the diaper when the bag is reversed by turning it inside out; one or more wet wipe pads within said bag; sealing means associated with said broad panel walls adjacent to said opening of the bag and tightly closing said opening so as to seal the wet wipe pad or pads against loss of moisture, said sealing means comprising a longitudinal tongue and receiving groove arrangement extending, respectively, along edge margins of the broad panel walls that are adjacent to the bag opening so as to tightly seal the bag when turned inside out to contain the diaper and the wet wipe pad or pads in soiled condition.

2. A disposable diaper and wet wipe pad package in accordance with claim 1, wherein the sealing means comprise tongue components on reverse faces, respectively, of the edge margin of one broad panel wall of the bag and groove components on reverse faces, respectively, of the edge margin of the opposite broad panel wall of the bag.

3. A disposable diaper and wet wipe pad package in accordance with claim 2, wherein the tongue components are on reverse faces, respectively, of the edge margin of the one broad panel wall that is fastened to the diaper.

4. A disposable diaper and wet wipe pad package in accordance with claim 1, wherein the sealing means comprise solely one set of coactive tongue and groove members positioned in confronting relationship on the inner faces, respectively, of the edge margins of the broad panel walls of the bag.

5. A disposable diaper and wet wipe pad package in accordance with claim 1, wherein the diaper-fastened wall of the bag provides the sole moisture proof backing for the diaper.

6. A disposable diaper and wet wipe pad package in accordance with claim 1, wherein the diaper-fastened wall of the bag overlies and is fastened to the normal moisture proof backing of the diaper to provide further moisture proof backing for the diaper.

7. A disposable diaper and wet wipe pad package in accordance with claim 1, wherein the end of the diaper opposite the diaper opening is formed as a flap that may be folded under the diaper opening in the reversed position of the bag to enhance closing of said opening against the escape of odor following sealing of the bundled diaper and wet wipe pad or pads.

8. A disposable diaper and wet wipe pad package in accordance with claim 1, wherein the end of the diaper opposite the diaper opening is formed as a flap that may be folded under the diaper opening in the reversed position of the bag to enhance closing of said opening against the escape of odor following sealing of the bundled diaper and wet wipe pad or pads.

* * * * *